(12) United States Patent
Wu et al.

(10) Patent No.: US 8,385,499 B2
(45) Date of Patent: Feb. 26, 2013

(54) 2D REFLECTOR AND COLLIMATOR STRUCTURE AND METHOD OF MANUFACTURING THEREOF

(75) Inventors: Zhaoping Wu, Shanghai (CN); Haochuan Jiang, Brookfield, WI (US); Joseph James Lacey, Cambridge, WI (US); James S. Vartuli, Rexford, NY (US); Yunfeng Sun, Beijing (CN); Qun Deng, Shanghai (CN); Xiaoye Wu, Rexford, NY (US); Kun Tao, Shanghai (CN); Zhaohui Yang, Shanghai (CN)

(73) Assignee: General Electric Company, Schenectady, NY (US)

( * ) Notice: Subject to any disclaimer, the term of this patent is extended or adjusted under 35 U.S.C. 154(b) by 630 days.

(21) Appl. No.: 12/647,603

(22) Filed: Dec. 28, 2009

(65) Prior Publication Data
US 2011/0158381 A1    Jun. 30, 2011

(51) Int. Cl.
*H05G 1/00* (2006.01)
*G21K 1/02* (2006.01)
*G21K 1/00* (2006.01)

(52) U.S. Cl. ................... 378/19; 378/147; 378/154
(58) Field of Classification Search ............. 378/4, 19, 378/147–155
See application file for complete search history.

(56) References Cited

U.S. PATENT DOCUMENTS

| | | | |
|---|---|---|---|
| 4,277,684 A | 7/1981 | Carson | |
| 4,792,686 A | 12/1988 | Karcher et al. | |
| 4,831,261 A | 5/1989 | Genna et al. | |
| 5,276,328 A | 1/1994 | Yoshida et al. | |
| 5,440,129 A | 8/1995 | Schmidt | |
| 5,799,057 A | 8/1998 | Hoffman et al. | |
| 6,452,186 B1 | 9/2002 | Wieczorek et al. | |
| 6,713,767 B2 | 3/2004 | Wieczorek et al. | |
| 6,749,761 B1 | 6/2004 | Andreaco et al. | |
| 6,793,857 B2 | 9/2004 | Otto | |
| 6,838,674 B2 | 1/2005 | Otto | |
| 6,894,282 B2 | 5/2005 | Freund et al. | |
| 7,141,812 B2 | 11/2006 | Appleby et al. | |
| 7,157,014 B1 | 1/2007 | Andreaco et al. | |
| 7,244,942 B2 | 7/2007 | Andreaco et al. | |
| 7,282,714 B2 | 10/2007 | Kobusch | |
| 2003/0202633 A1* | 10/2003 | Hoffman | 378/147 |
| 2004/0140431 A1 | 7/2004 | Schmand et al. | |
| 2004/0227092 A1 | 11/2004 | Ratzmann et al. | |

(Continued)

FOREIGN PATENT DOCUMENTS

DE    19753268 A1    7/1998
DE    19849958 A1    5/1999

(Continued)

*Primary Examiner* — Irakli Kiknadze
(74) *Attorney, Agent, or Firm* — Ziolkowski Patent Solutions Group, SC

(57) ABSTRACT

A two dimensional collimator assembly and method of manufacturing thereof is disclosed. The collimator assembly includes a wall structure constructed to form a two dimensional array of channels to collimate x-rays. The wall structure further includes a first portion positioned proximate the object to be scanned and configured to absorb scattered x-rays and a second portion formed integrally with the first portion and extending out from the first portion away from the object to be scanned. The first portion of the wall structure has a height greater than a height of the second portion of the wall structure. The second portion of the wall structure includes a reflective material coated thereon in each of the channels forming the two dimensional array of channels.

21 Claims, 9 Drawing Sheets

U.S. PATENT DOCUMENTS

2005/0281701 A1* 12/2005 Lynch et al. .................. 419/10
2007/0025519 A1* 2/2007 Vogtmeier et al. ............ 378/149

FOREIGN PATENT DOCUMENTS

| | | | |
|---|---|---|---|
| DE | 19750935 | A1 | 6/1999 |
| EP | 0447879 | A2 | 9/1991 |
| WO | 2004072680 | A2 | 8/2004 |
| WO | 2006065441 | A2 | 6/2006 |
| WO | 2007080535 | A2 | 7/2007 |

* cited by examiner

2D REFLECTOR AND COLLIMATOR STRUCTURE AND METHOD OF MANUFACTURING THEREOF

BACKGROUND OF THE INVENTION

The invention relates generally to collimators for use in diagnostic imaging and, more particularly, to a two dimensional reflector and collimator assembly and method of manufacturing thereof.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator for collimating x-ray beams received at the detector, a scintillator for converting x-rays to light energy adjacent the collimator, and photodiodes for receiving the light energy from the adjacent scintillator and producing electrical signals therefrom. The outputs of the photodiodes are then transmitted to the data processing system for image reconstruction.

As stated above, typical x-ray detectors include a collimator for collimating x-ray beams such that collection of scattered x-rays is minimized. As such, the collimators operate to attenuate off-angle scattered x-rays from being detected by a scintillator cell. Reducing this scattering reduces noise in the signal and improves the final reconstructed image. Therefore, it is necessary that the scintillator array and the collimator, typically plates extending along one dimension above the scintillator array, are uniformly aligned. That is, exact mechanical alignment is required between the collimator plates and the cast reflector lines in the array of scintillators.

Known manufacturing processes attempt this exact alignment by constructing a continuous collimator that is sized to dimensionally match the width and length of the entire detector array. That is, the collimator plates are arranged or arrayed in a continuous consistent pattern or pitch that spans the entire detector length and is placed and attached to the detector rail structure. As such, individual scintillator arrays or packs must then be exactly aligned to the continuous collimator to ensure that all scintillator cells and collimator cells are aligned exactly; otherwise the collimator must be discarded or repaired, or the scintillator packs must be discarded. This process requires excessively tight tolerancing and requires great operator skill and patience to assemble. Accordingly, these known processes are susceptible to waste of parts, material, and labor.

A known CT detector 1 fabricated according to known manufacturing processes is shown in FIG. 1. The CT detector 1 includes a series of tungsten collimator plates 2 configured and position to collimate, in one dimension, x-rays projected toward scintillator cells 3 of a scintillator array 4. As shown, each of the collimator plates 2 is generally aligned with a reflector line 5 disposed between adjacent scintillators 3. The reflector lines 5 prevent light from being emitted between adjacent scintillators. The scintillator array is coupled to a photodiode array 6 that detects light emissions from the scintillator array and transmits corresponding electrical signals to a data acquisition system for signal processing. As readily shown, the collimator plates are not integrated with the individual scintillator elements 3. That is, an air gap 7 exists between the collimator plates and the scintillator cells 3. The air gap 7 typically results in a separation between the collimator plates and the scintillator array of approximately two to four thousandths of an inch. This air gap occurs as a result of the manufacturing process whereupon the collimator plates are formed as a single collimator assembly that accepts and aligns an array of scintillators. The air gap, however, makes the CT detector susceptible to x-rays received between two collimator plates impinging upon an adjacent scintillator thereby resulting in undesirable anomalies in the final reconstructed CT image. Additionally, and as shown in FIG. 1, the collimator plates 2 serve to collimate x-rays projected toward scintillator cells 3 in only one dimension, which places limitations on the effectiveness of the collimator assembly.

Therefore, it would be desirable to design a reflector and collimator assembly and method of manufacturing thereof that provides for easy alignment between the scintillator array and the collimator assembly and that effectively prevents cross-talk between adjacent scintillators. It would further be desirable to provide a reflector and collimator assembly and method of manufacturing thereof that provides for two-dimensional collimation of x-rays.

BRIEF DESCRIPTION OF THE INVENTION

Embodiments of the invention are directed to a two dimensional reflector and collimator assembly and a method of manufacturing thereof.

In accordance with one aspect of the invention, a collimator assembly for a CT imaging system positioned between an object to be scanned and a CT detector includes a wall structure constructed to form a two dimensional array of channels to collimate x-rays. The wall structure further includes a first portion positioned proximate the object to be scanned and configured to absorb scattered x-rays and a second portion formed integrally with the first portion and extending out from the first portion away from the object to be scanned, with a height of the first portion being greater than a height of the second portion. The second portion of the wall structure includes a reflective material coated on the wall structure in each of the channels forming the two dimensional array of channels.

In accordance with another aspect of the invention, a method of fabricating a collimator assembly for a CT medical imaging system includes providing a powder material having a density and atomic number that is sufficient to substantially absorb x-rays, providing a binding agent, and mixing the powder material and the binding agent to form a collimator material. The method also includes the step of extruding the collimator material through a collimator extrusion die to form a honeycomb collimator assembly, with the honeycomb collimator assembly comprising a two dimensional array of channels formed therethrough.

In accordance with yet another aspect of the invention, a CT imaging system includes a rotatable gantry having an opening to receive an object to be scanned, a high frequency electromagnetic energy projection source configured to project a high frequency electromagnetic energy beam toward the object, and a scintillator array positioned on the gantry opposite the high frequency electromagnetic energy projection source, the scintillator array including a plurality of scintillator cells configured to detect high frequency electromagnetic energy passing through the object. The CT imaging system also includes a collimator assembly positioned between the object and the scintillator array, with the collimator assembly comprising a honeycomb wall structure configured to form a two dimensional array of channels to collimate x-rays. A portion of the collimator assembly is formed about the scintillator array such that each of the plurality of scintillator cells is housed within a respective channel in the two dimensional array of channels.

Various other features and advantages will be made apparent from the following detailed description and the drawings.

BRIEF DESCRIPTION OF THE DRAWINGS

The drawings illustrate preferred embodiments presently contemplated for carrying out the invention.

In the drawings.

DETAILED DESCRIPTION OF THE PREFERRED EMBODIMENT

The operating environment of the invention is described with respect to a sixty-four-slice computed tomography (CT) system. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic energy. The invention will be described with respect to a "third generation" CT scanner, but is equally applicable with other CT systems.

Figure 2:
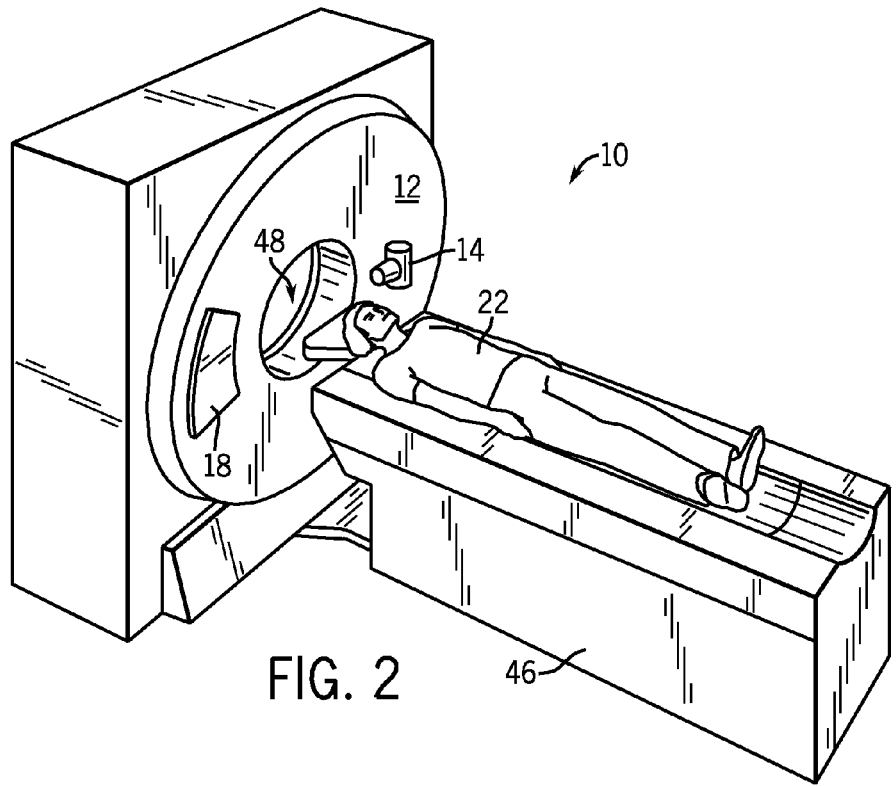
FIG. 2 is a pictorial view of a CT imaging system.
Figure 3:
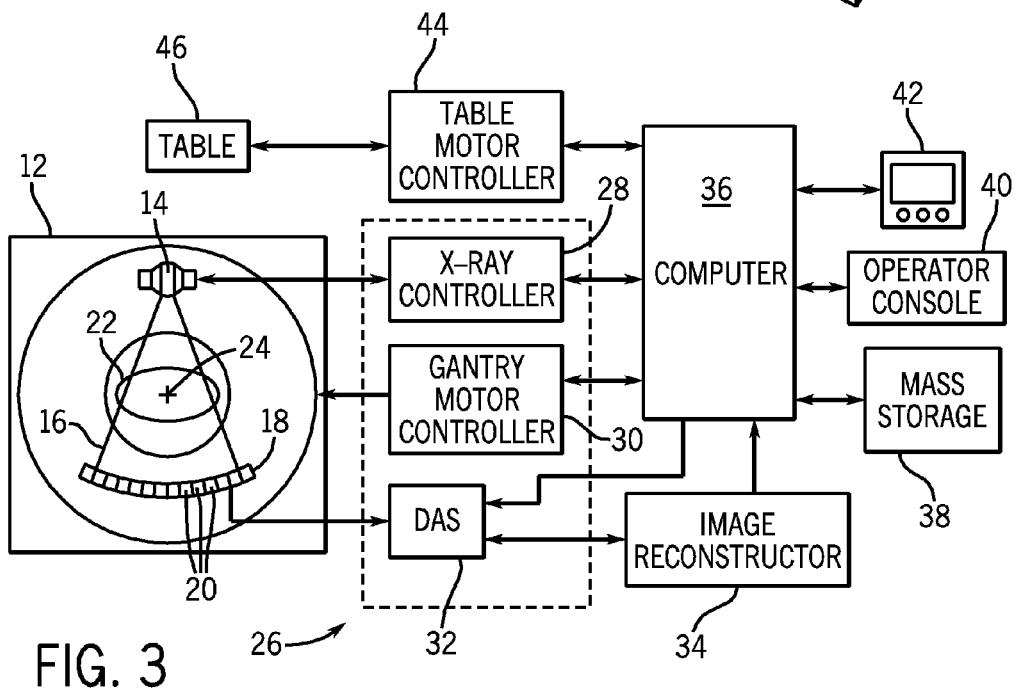
FIG. 3 is a block schematic diagram of the system illustrated in FIG. 2.

Referring to FIG. 2, a computed tomography (CT) imaging system 10 is shown as including a gantry 12 representative of a "third generation" CT scanner. Gantry 12 has an x-ray source 14 that projects a beam of x-rays toward a detector assembly or collimator 18 on the opposite side of the gantry 12. Referring now to FIG. 3, detector assembly 18 is formed by a plurality of detectors 20 and data acquisition systems (DAS) 32. The plurality of detectors 20 sense the projected x-rays 16 that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves patients 22 through a gantry opening 48 of FIG. 2 in whole or in part.

Figure 4:
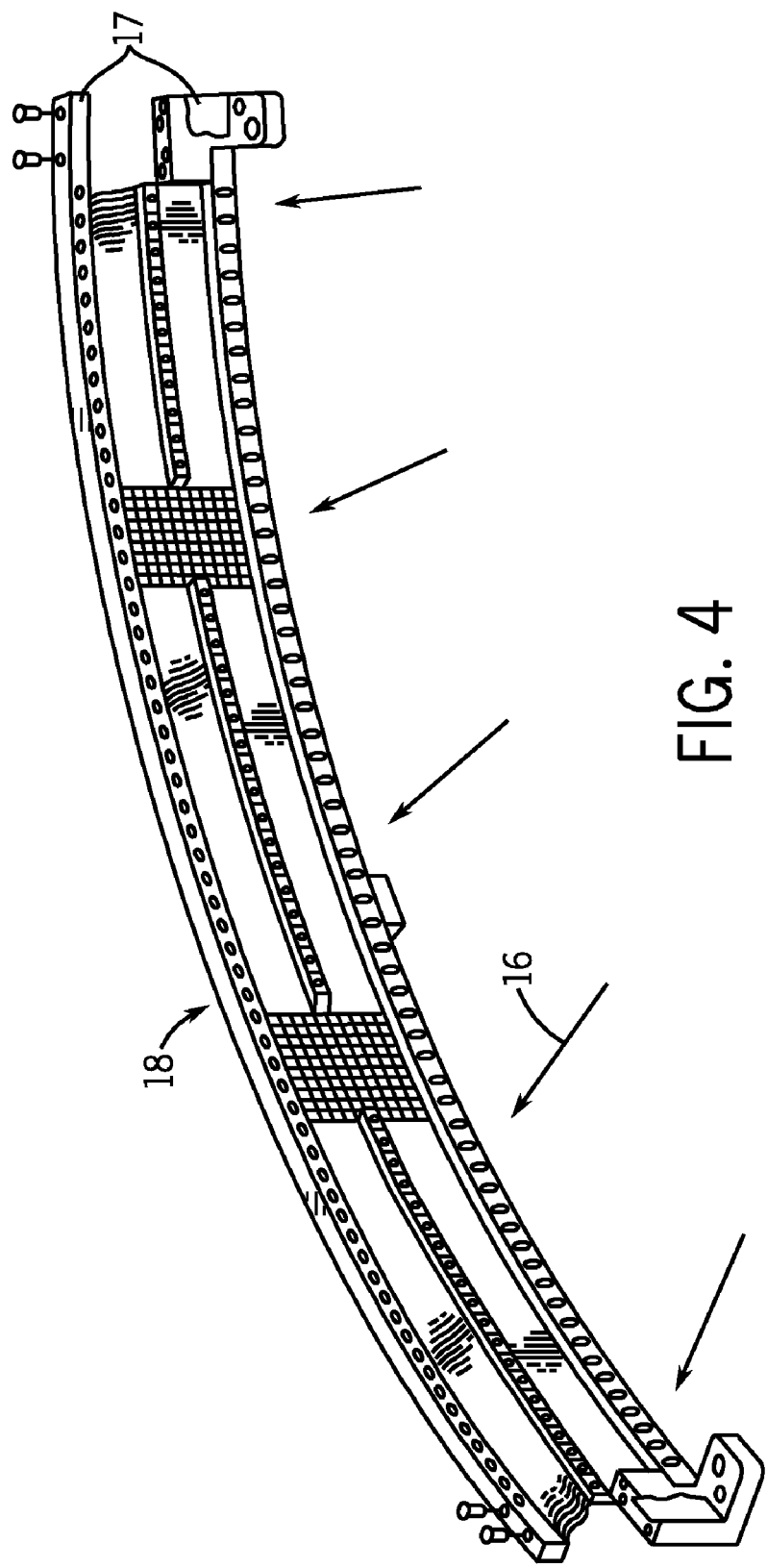
FIG. 4 is a perspective view of one embodiment of a CT system detector assembly.

As shown in FIG. 4, detector assembly 18 includes rails 17 having a plurality of reflector-collimator assemblies 19, hereinafter generally referred to as "collimator assemblies," placed thereon and having detectors 20 secured thereto. Collimator assemblies 19 are positioned on rail to collimate x-rays 16 before such beams impinge upon, for instance, detector elements 50 of FIG. 5 positioned within the collimator assembly. In one embodiment, detector assembly 18 includes 57 detectors 20, each detector 20 having an array size of 64×16 of pixel elements 50. As a result, detector assembly 18 has 64 rows and 912 columns (16×57 detectors) which allows 64 simultaneous slices of data to be collected with each rotation of gantry 12.

Figure 5:
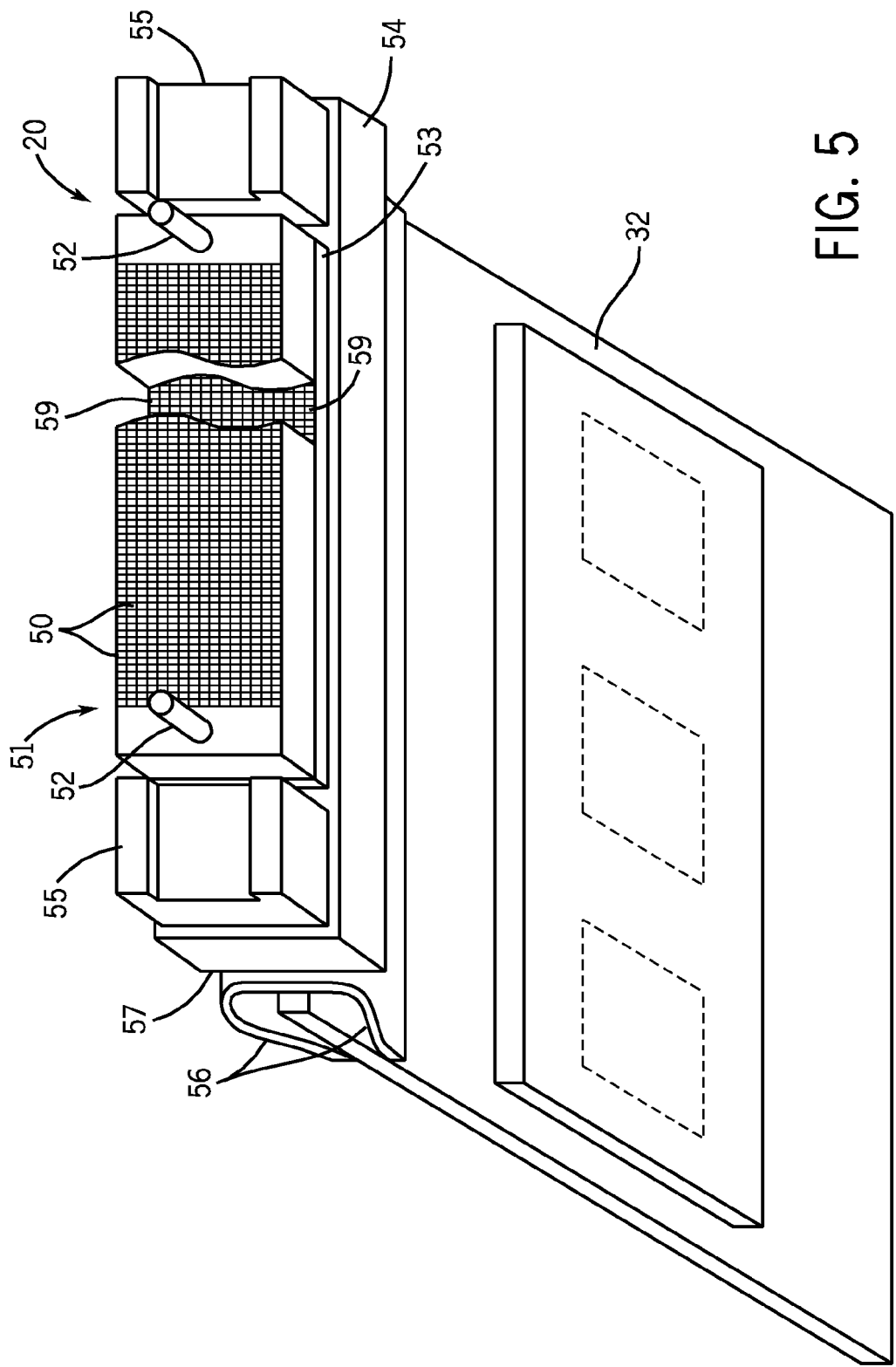
FIG. 5 is a perspective view of one embodiment of a detector.

A detector 20 is shown in FIG. 5 for use with embodiments of the invention. Each detector 20 includes a number of detector elements 50 (i.e., scintillator pixels) forming an array 51 (i.e., scintillator array). Scintillator array 51 is optically coupled to a backlit diode array 53 having a plurality of diodes 59, with backlit diode array 53 in turn being positioned on, and electrically coupled to, multi-layer substrate 54. While scintillator array 51 is described as forming part of detector 20, scintillator pixels 50 are in fact positioned within a portion of collimator assembly 19, which is then positioned relative to diode array 53 and the remainder of detector 20, as is explained in greater detail below.

As further shown in FIG. 5, detectors 20 also include pins 52 positioned relative to scintillator array 51 and spacers 55 positioned on multi-layer substrate 54. Flex circuits 56 are attached to face 57 of multi-layer substrate 54 and to DAS 32. Detectors 20 are positioned within detector assembly 18 by use of pins 52. In the operation of one embodiment, x-rays impinging within detector elements 50 generate photons which traverse scintillator array 51, thereby generating an analog signal which is detected on a diode within backlit diode array 53. The analog signal generated is carried through multi-layer substrate 54, through flex circuits 56, to DAS 32 wherein the analog signal is converted to a digital signal.

Figure 6:
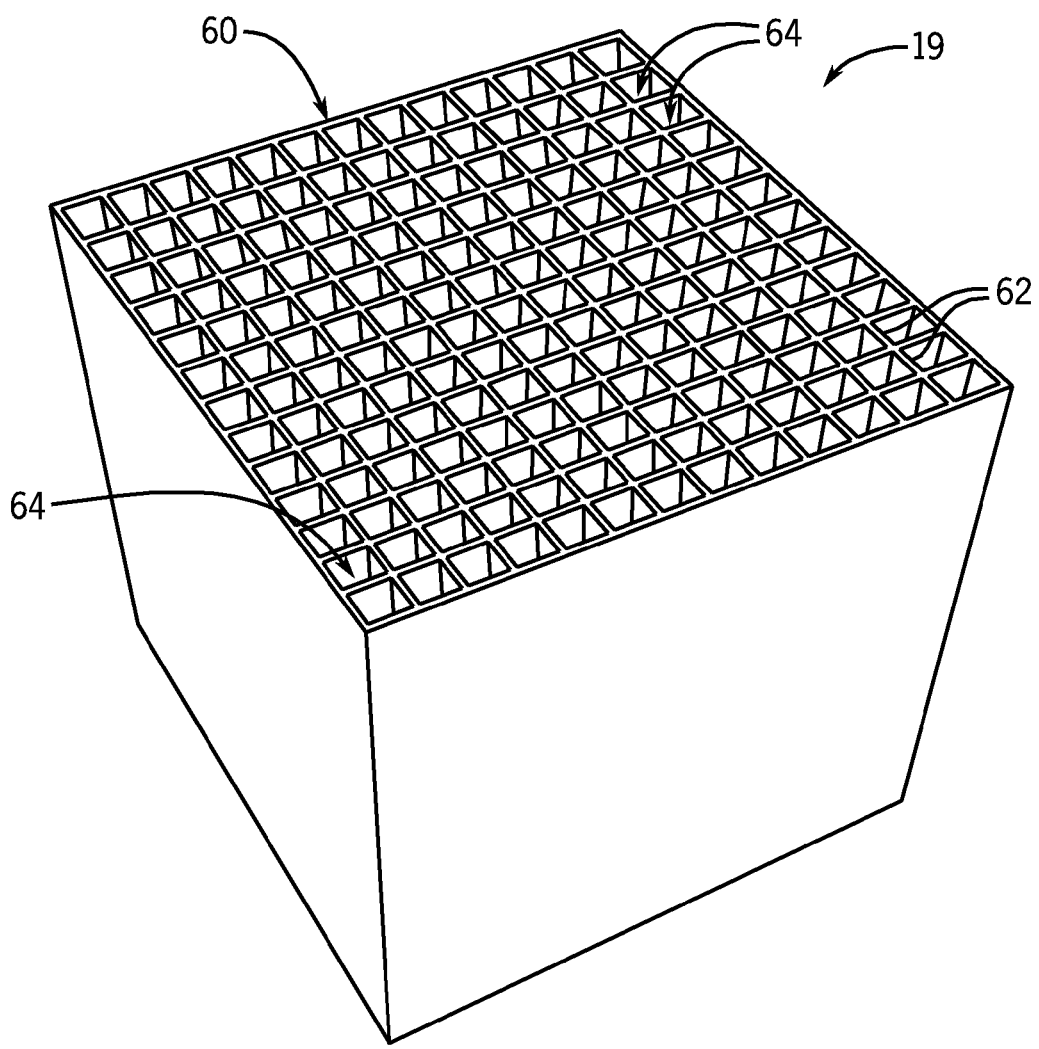
FIG. 6 is a perspective view of a collimator assembly according to an embodiment of the invention.

Referring now to FIG. 6, collimator assembly 19 is shown according to an embodiment of the present invention. Collimator assembly 19 is configured as a "two dimensional collimator" in that a wall structure 60 forming the collimator assembly 19 has a honeycomb structure. A plurality of walls 62 forming wall structure 60 are arranged to define a two dimensional array of channels 64 that collimate x-rays attenuated by subject 22, for example, prior to the x-rays impinging upon detector 20 (FIG. 5). The wall structure 60 of collimator assembly 19 is formed and arranged such that a pitch of channels 64 is identical to a pitch of detector elements 50 (FIG. 5), which according to one embodiment are formed as scintillator pixels. According to an exemplary embodiment, walls 62 of wall structure 60 are thus formed to have a thickness of 0.10 to 0.20 mm and walls 62 are spaced apart to have a pitch of 1.0 to 1.2 mm, for example.

According to an exemplary embodiment of the invention, wall structure 60 of collimator assembly 19 is composed of a mixed metal and binder material having a density and atomic number that is sufficient to substantially absorb x-rays. According to an exemplary embodiment, a powder composed of a heavy metal, heavy metal alloy powder, or heavy metal oxide is mixed with an organic polymer or thermoplastic material to provide a mixed collimator forming material, hereinafter referred to generally as a "mixed metal-binder material." Thus, wall structure 60 may be formed of Pb, Ta, W, Au, or Pt powder, for example, that is bonded with an organic polymer or thermoplastic material. The mixed metal-binder material is extruded through a collimator extrusion die (not shown) to form the wall structure 60 and the channels 64 therein.

Figure 7:
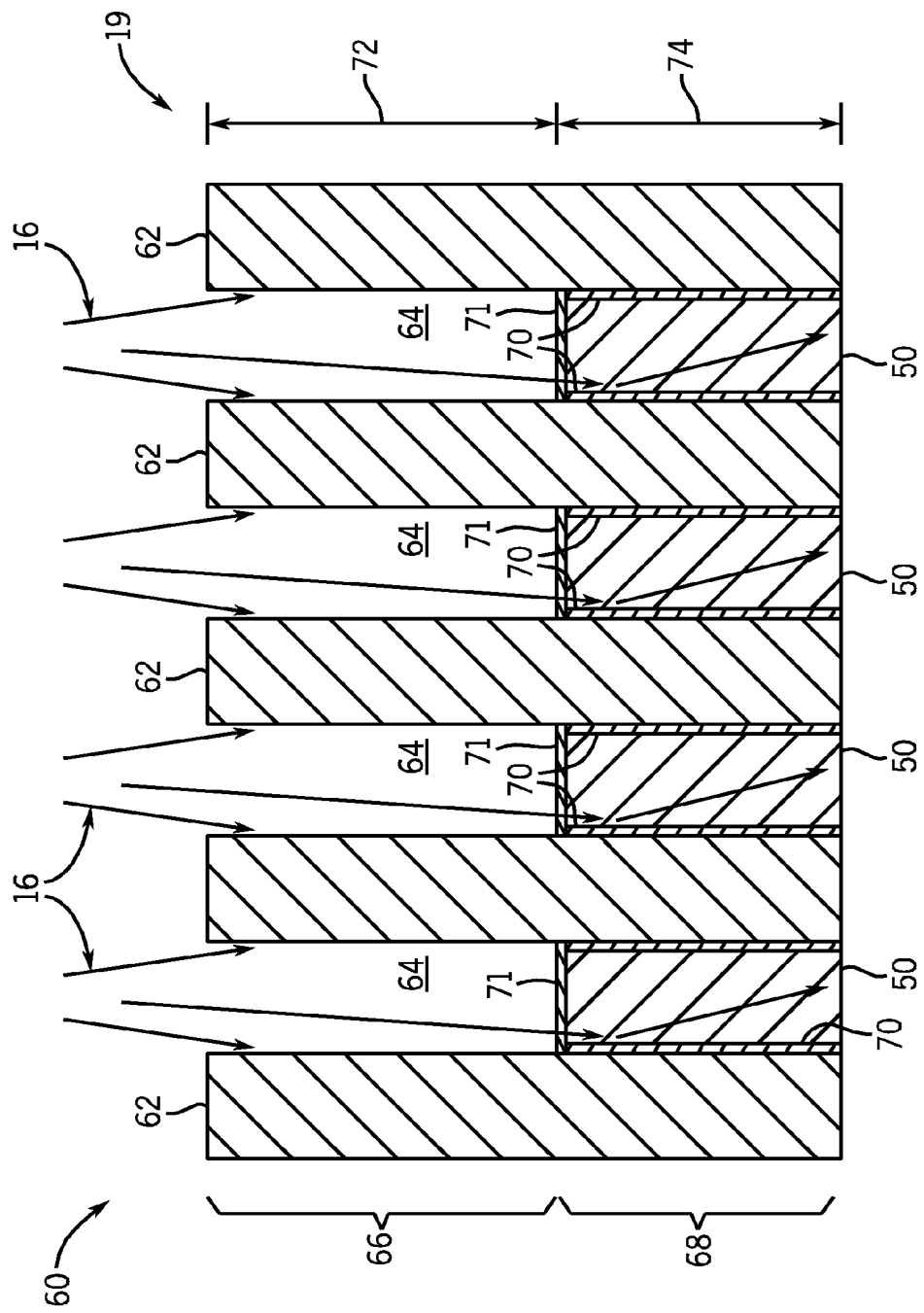
FIG. 7 is a cross-sectional view of the collimator assembly of FIG. 6 along with scintillator pixels positioned therein.

A cross-sectional view of a portion of collimator assembly 19 is shown in FIG. 7. While collimator assembly 19 is shown as having a wall structure 60 defining only four channels 64, it is noted that FIG. 7 is for illustrative purposes only and that collimator assembly 19 would be formed to include a wall structure 60 that defines a greater number of channels arranged in a two-dimensional array, such as shown in FIG. 6. As shown in FIG. 7, wall structure 60 is generally defined as including a first portion 66 and a second portion 68 stacked in a vertical arrangement, according to an exemplary embodiment of the invention. While wall structure 60 of collimator assembly 19 is formed as an integral structure, and thus first and second portions 66, 68 are in fact formed as a single unitary structure, the first portion 66 of the collimator assembly 19 is identified as functioning as a collimator to collimate x-rays, while the second portion 68 is identified as functioning as a reflective grid that separates individual detector cells 50 (i.e., scintillator pixels) from each other to prevent cross-talk therebetween. As shown in FIG. 7, scintillator pixels 50 having a reflective material 71 coated on a top surface thereof are positioned within second portion 68 of wall structure 60, such that each scintillator pixel is housed within a respective channel 64 of the array of channels in collimator assembly 19.

Figure 1:
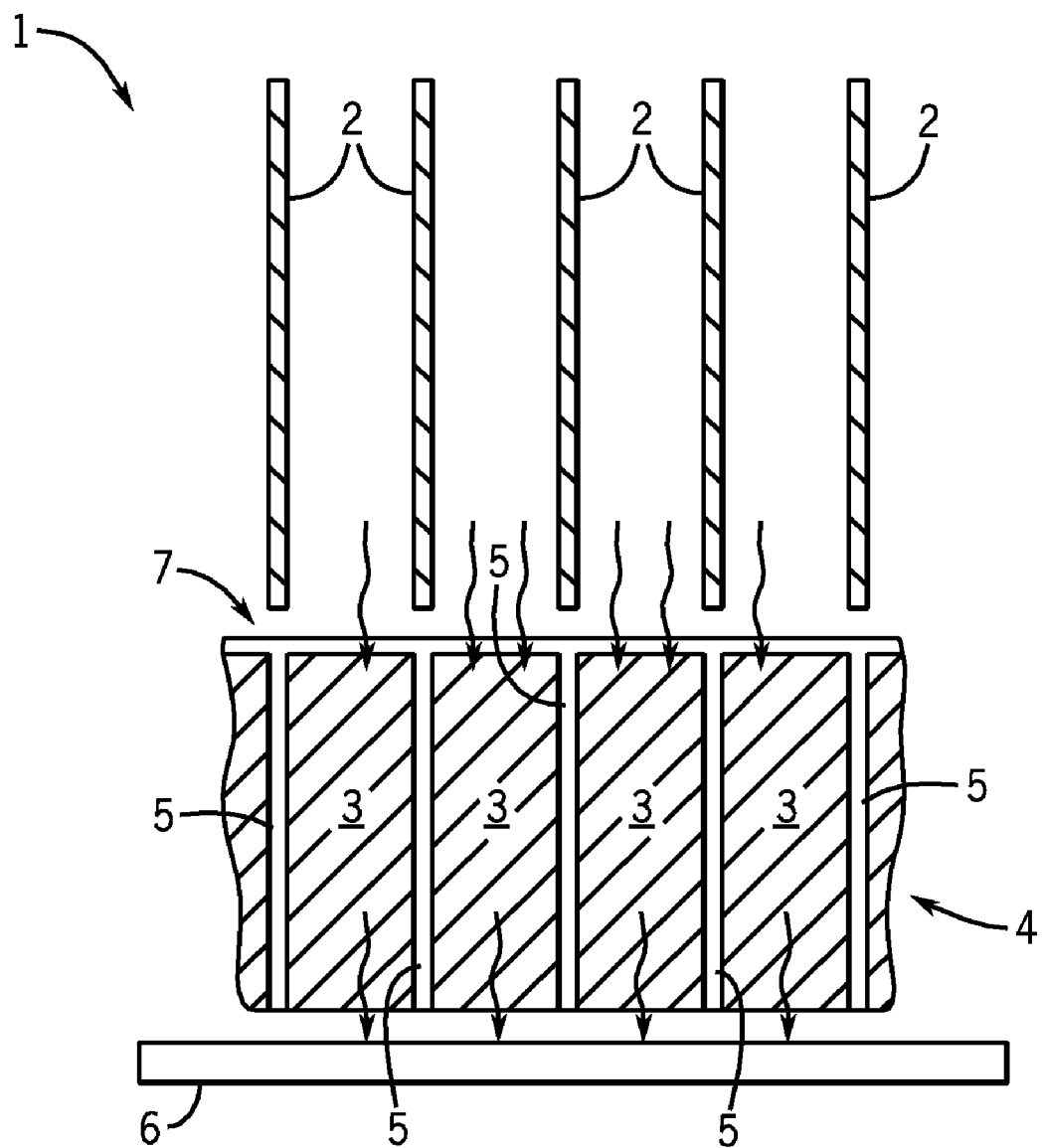
FIG. 1 is a cross-sectional view of a prior art CT detector having a collimator aligned with a scintillator array.

The first portion 66 of collimator assembly 19 is positioned proximate subject 22 (FIG. 1) so as to receive x-rays 16 attenuated therefrom. As set forth above, wall structure 60 is formed of a mixed metal-binder material having a density and atomic number that is sufficient to substantially absorb x-rays. Thus, as shown in FIG. 7, x-rays entering collimator assembly 19 at an undesired scatter angle are absorbed by first portion 66 of wall structure 60. The second portion 68 of wall structure 60 extends out from the first portion 66 away from the subject (i.e., downstream of x-rays) so as to receive x-rays 16 that pass through first portion 66. The second portion 68 of wall structure 60 includes a reflective material 70 that is coated on walls 62 such that each of the channels 64 forming the two dimensional array of channels is coated with the reflective material 70. The reflective material 70 and 71 may be composed of Al, Ag, Au, $TiO_2$, $BaSO_4$, and MgO, or some other similar material that acts to reflect light thereoff. That is, as collimated x-rays 16 pass through first portion 66 of wall structure 60 and impinge on the scintillator material of detector cells 50 housed in second portion 68 of wall structure 60, photons are generated. The reflective material 70 coated on walls 62 and reflective material 71 coated on the top of scintillator pixels 50 act to reflect these photons, such that they are trapped within a particular detector cell 50, allowing for readout thereof by diode array 53 (FIG. 5) without cross-talk interference from adjacent detector cells.

As shown in FIG. 7, first portion 66 of wall structure 60 is formed to have a height 72 that is greater than a height 74 of second portion 68 of wall structure 60. According to an exemplary embodiment, a height of first portion 66 is at least twice a height of second portion 68. Thus, a height of first portion 66 may be approximately 8 mm and a height of second portion 68 may be approximately 1.5-3 mm, for example. A height ratio between first and second portions 66, 68 such as the one set forth above provides for first portion 66 of wall structure 60 to properly collimate x-rays 16 passing therethrough, while still allowing for a desired dose of x-rays to reach detector cells 50.

Figure 8:
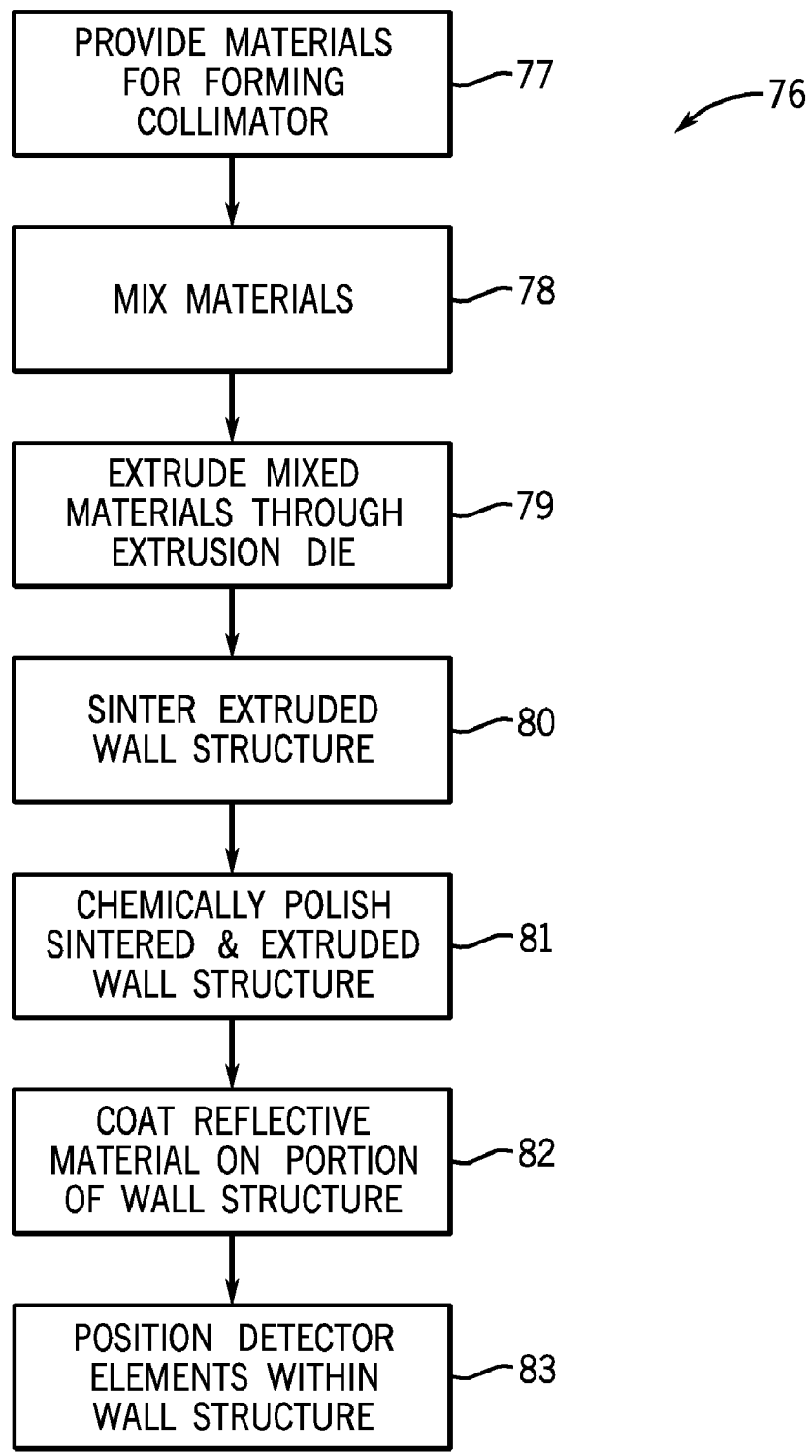
FIG. 8 is a flow-chart illustrating a technique for manufacturing a collimator assembly according to an embodiment of the invention.

Referring now to FIG. 8, a technique 76 for manufacturing collimator assembly 19 is set forth according to an embodiment of the invention. The technique 76 begins with the providing of materials for forming the collimator assembly at block 77. The materials include a metal or ceramic material having a density and atomic number that is sufficient to substantially absorb x-rays, as well as a binder material that is mixed with the metal/ceramic material in order to form a collimator assembly having sufficient rigidity and structural strength. According to an exemplary embodiment, the metal/ceramic material is in the form of a powder composed of a heavy metal, heavy metal alloy, heavy metal oxide, or ceramic, examples of which include Pb, Ta, W, Au, Pt, $WO_3$, $BiO_3$, $Ta_2O_5$, PbO, and heavy rare earth metal oxides such as $Gd_2O_3$, $Lu_2O_3$, etc. The metal/ceramic powder is then mixed with the binder material at block 78, which according to the embodiment of FIG. 8, is in the form of an organic polymer such as silicone, epoxy, or polyimide, for example. A mixed metal-binder material is formed upon combination of the metal/ceramic powder and the binding material. The mixed metal-binder material is extruded through a collimator extrusion die at block 79 to form the honeycomb wall structure of the collimator assembly having the two-dimensional array of channels therein.

In a next step of the manufacturing technique 76, the extruded wall structure is sintered at block 80 so as to increase the mechanical strength of the wall structure to a desired level. In order to reduce surface roughness of the wall structure resulting from the sintering process, the wall structure is chemically polished at block 81. Upon chemical polishing of the wall structure, a reflective material is coated on the wall structure within each of the channels at block 82. According to an exemplary embodiment, the reflective material is coated on only a bottom or "second" portion of each channel (i.e., a portion adjacent to detector 20). The reflective material may be composed of Al, Ag, Au, $TiO_2$, $BaSO_4$, and MgO, or some other similar material that acts to reflect photons (i.e., light) thereoff.

The manufacturing technique 76 continues with positioning of detector elements relative to the collimator assembly at block 83. Detector elements, in the form of scintillator pixels or crystals having a reflective material coated on a top surface thereof, are positioned relative to the collimator assembly such that an individual detector element is positioned within each of the channels in the collimator assembly. That is, a scintillator pixel/crystal is positioned within each of the channels in the collimator assembly in the bottom or "second" portion of the channel, such that the scintillator pixel/crystal is within that portion of the channel that has been coated with the reflective material. Accordingly, as x-rays pass through upper or "first" portion of the wall structure to impinge on the scintillator material housed in the bottom/second portion of the channel, photons generated by the scintillator material will be contained in each pixel by the reflection provided by the reflective material coated within the channels of the wall structure and on the top of the scintillator pixels.

Figure 9:
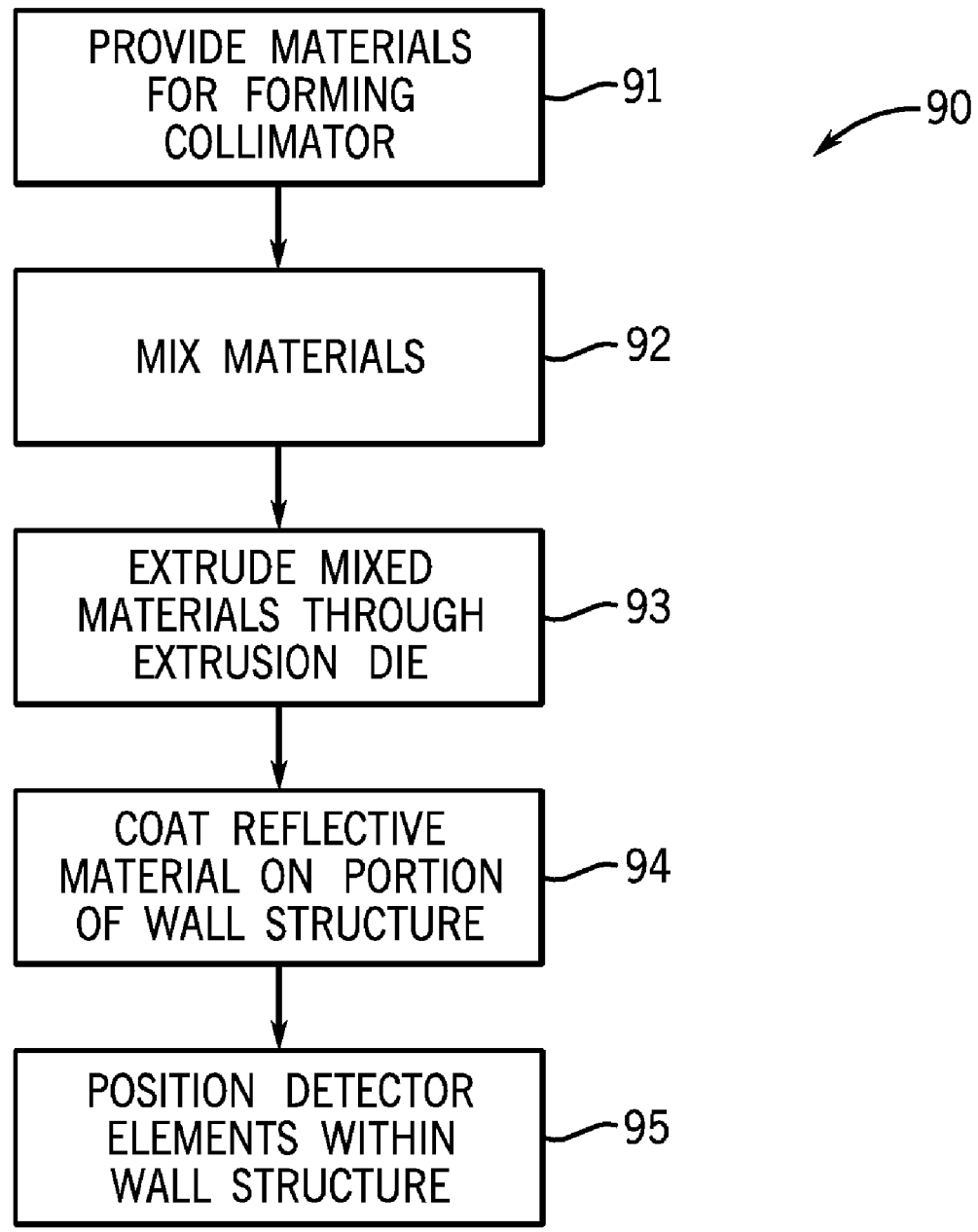
FIG. 9 is a flow-chart illustrating a technique for manufacturing a collimator assembly according to another embodiment of the invention.

Referring now to FIG. 9, a technique 90 for manufacturing collimator assembly 19 is set forth according to another embodiment of the invention. The technique 90 begins with the providing of materials for forming the collimator assembly at block 91. The materials include a metal or ceramic material having a density and atomic number that is sufficient to substantially absorb x-rays, as well as a binder material that is mixed with the metal/ceramic material in order to form a collimator assembly having sufficient rigidity and structural strength. According to an exemplary embodiment, the metal/ceramic material is in the form of a powder composed of a heavy metal, heavy metal alloy, heavy metal oxide, or ceramic. The metal/ceramic powder is then mixed with the binder material at block 92, which according to the embodiment of FIG. 9 is in the form of a thermoplastic material. A mixed metal-binder material is formed upon combination of the metal/ceramic powder and the thermoplastic. The mixed metal-binder material is extruded through a collimator extrusion die at block 93 to form the honeycomb wall structure of the collimator assembly having the two-dimensional array of channels therein.

Based on the structural rigidity and strength provided by the thermoplastic binding material, no sintering or further strengthening process need be applied to the extruded wall structure. Thus, the manufacturing technique continues with the application of a reflective material on the wall structure within each of the channels at block 94. According to an exemplary embodiment, the reflective material is coated on only a bottom or "second" portion of each channel (i.e., a portion adjacent to detector 20). The reflective material may be composed of Al, Ag, Au, $TiO_2$, $BaSO_4$, and MgO, or some other similar material that acts to reflect photons (i.e., light) thereoff.

The manufacturing technique continues with positioning of detector elements relative to the collimator assembly at block 95. Detector elements, in the form of scintillator pixels or crystals having a reflective material coated on a top surface thereof, are positioned relative to the collimator assembly such that an individual detector element is positioned within each of the channels in the collimator assembly. That is, a scintillator pixel/crystal is positioned within each of the channels in the collimator assembly in the bottom or "second" portion of the channel, such that the scintillator pixel/crystal is within that portion of the channel that has been coated with the reflective material. Accordingly, as x-rays pass through upper or "first" portion of the wall structure to impinge on the scintillator material housed in the bottom/second portion of the channel, photons generated by the scintillator material will be contained in each pixel by the reflection provided by the reflective material coated within the channels of the wall structure and on the top of the scintillator pixels.

Beneficially, the manufacturing techniques shown and described in each of FIGS. 8 and 9 allow for fine-tuning of the properties of the collimator assembly. That is, the properties of the collimator assembly can be tuned by the die design, the ratio of metal/ceramic to binder in the collimator formation mixture, and the thickness and height of the wall of the honeycomb collimator assembly. Additionally, the manufacturing techniques shown and described in each of FIGS. 8 and 9 eliminate an air gap that typically exists between collimator plates and scintillator cells by positioning the scintillator cells/pixels into the two-dimensional array of channels in the collimator assembly. Furthermore, the manufacturing techniques shown and described in each of FIGS. 8 and 9 provide for a collimator assembly that allows for higher spatial resolution in generated CT images.

Figure 10:
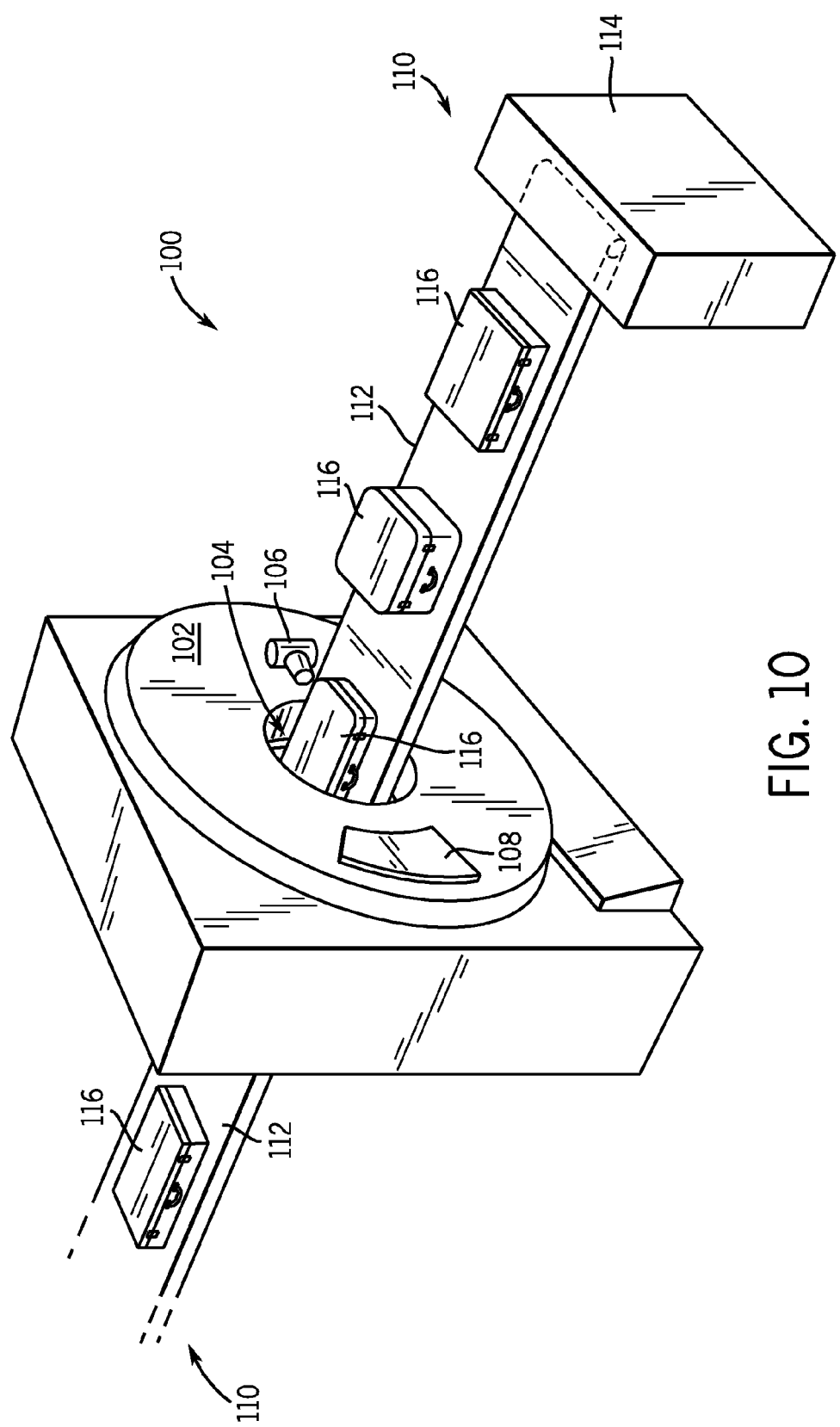
FIG. 10 is a pictorial view of a CT system for use with a non-invasive package inspection system.

Referring now to FIG. 10, a package/baggage inspection system 100 is shown that can incorporate a collimator assembly 19 (FIGS. 6 and 7) and that includes a rotatable gantry 102 having an opening 104 therein through which packages or pieces of baggage may pass. The rotatable gantry 102 houses a high frequency electromagnetic energy source 106 as well as a detector assembly 108 having scintillator arrays comprised of scintillator cells similar to that shown in FIG. 6 or 7. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

Therefore, according to one embodiment of the invention, a collimator assembly for a CT imaging system positioned between an object to be scanned and a CT detector includes a wall structure constructed to form a two dimensional array of channels to collimate x-rays. The wall structure further includes a first portion positioned proximate the object to be scanned and configured to absorb scattered x-rays and a second portion formed integrally with the first portion and extending out from the first portion away from the object to be scanned, with a height of the first portion being greater than a height of the second portion. The second portion of the wall structure includes a reflective material coated on the wall structure in each of the channels forming the two dimensional array of channels.

According to another embodiment of the invention, a method of fabricating a collimator assembly for a CT medical imaging system includes providing a powder material having a density and atomic number that is sufficient to substantially absorb x-rays, providing a binding agent, and mixing the powder material and the binding agent to form a collimator material. The method also includes the step of extruding the collimator material through a collimator extrusion die to form a honeycomb collimator assembly, with the honeycomb collimator assembly comprising a two dimensional array of channels formed therethrough.

According to yet another embodiment of the invention, a CT imaging system includes a rotatable gantry having an opening to receive an object to be scanned, a high frequency electromagnetic energy projection source configured to project a high frequency electromagnetic energy beam toward the object, and a scintillator array positioned on the gantry opposite the high frequency electromagnetic energy projection source, the scintillator array including a plurality of scintillator cells configured to detect high frequency electromagnetic energy passing through the object. The CT imaging system also includes a collimator assembly positioned between the object and the scintillator array, with the collimator assembly comprising a honeycomb wall structure configured to form a two dimensional array of channels to collimate x-rays. A portion of the collimator assembly is formed about the scintillator array such that each of the plurality of scintillator cells is housed within a respective channel in the two dimensional array of channels.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A collimator assembly for a CT imaging system positioned between an object to be scanned and a CT detector, the collimator assembly comprising:
a wall structure constructed to form a two dimensional array of channels to collimate x-rays, wherein the wall structure comprises:
a first portion positioned proximate the object to be scanned and configured to absorb scattered x-rays; and
a second portion formed integrally with the first portion and extending out from the first portion away from the object to be scanned, the second portion including a reflective material coated on the wall structure in each of the channels forming the two dimensional array of channels;
wherein a height of the first portion is greater than a height of the second portion.

2. The collimator assembly of claim 1 wherein the wall structure is composed of a binder material and a powder material having a density and atomic number that is sufficient to substantially absorb x-rays.

3. The collimator assembly of claim 2 wherein the binder material comprises one of an organic polymer and a thermoplastic material.

4. The collimator assembly of claim 2 wherein the powder material comprises one or more of a heavy metal powder, a heavy metal alloy powder, a heavy metal oxide powder, and a ceramic powder.

5. The collimator assembly of claim 2 wherein the wall structure comprises an extruded wall structure formed from the binder material and the powder material.

6. The collimator assembly of claim 5 wherein the extruded wall structure comprises a sintered wall structure having a chemically polished finish.

7. The collimator assembly of claim 1 further comprising a scintillator array positioned in the second portion of the wall structure, the scintillator array comprising a plurality of scintillator elements arranged such that each scintillator element is housed within a respective channel in the two dimensional array of channels, and wherein each of the plurality of scintillator elements has a reflective material coated on a top surface thereof.

8. The collimator assembly of claim 1 wherein the reflective material comprises one of Al, Ag, Au, $TiO_2$, $BaSO_4$, and MgO.

9. The collimator assembly of claim 1 wherein a height of the first portion is at least twice a height of the second portion.

10. The collimator assembly of claim 9 wherein a height of the first portion is approximately 8 mm and a height of the second portion is approximately 3 mm.

11. A method of fabricating a collimator assembly for a CT medical imaging system, the method comprising:
providing a powder material having a density and atomic number that is sufficient to substantially absorb x-rays;
providing a binding agent;
mixing the powder material and the binding agent to form a collimator material;
extruding the collimator material through a collimator extrusion die to form a honeycomb collimator assembly, the honeycomb collimator assembly comprising a two dimensional array of channels formed therethrough and
coating a reflective material on a portion of the honeycomb collimator assembly.

12. The method of claim 11 further comprising:
sintering the extruded honeycomb collimator assembly; and
chemically polishing the sintered honeycomb collimator assembly.

13. The method of claim 11 wherein coating the reflective material on a portion of the honeycomb collimator assembly comprises coating the reflective material on a portion of each of the channels forming the two dimensional array of channels.

14. The method of claim 13 further comprising positioning a scintillator pixel in each channel of the two dimensional array of channels, the scintillator pixel including a reflective material coated on a top surface thereof and being positioned in the portion of the channel having the reflective material coated thereon.

15. A CT imaging system comprising:
a rotatable gantry having an opening to receive an object to be scanned;
a high frequency electromagnetic energy projection source configured to project a high frequency electromagnetic energy beam toward the object;
a scintillator array positioned on the gantry opposite the high frequency electromagnetic energy projection source, the scintillator array including a plurality of scintillator cells configured to detect high frequency electromagnetic energy passing through the object; and
a collimator assembly positioned between the object and the scintillator array, the collimator assembly comprising a honeycomb wall structure configured to form a two dimensional array of channels to collimate x-rays;
wherein a portion of the collimator assembly is formed about the scintillator array such that each of the plurality of scintillator cells is housed within a respective channel in the two dimensional array of channels.

16. The CT imaging system of claim 15 wherein the honeycomb wall structure comprises:
a first portion configured to absorb scattered x-rays that impinge upon the honeycomb wall structure thereof; and
a second portion formed integrally with the first portion and extending out from the first portion away from the object to be scanned, the second portion including a reflective material coated on the honeycomb wall structure in each of the channels forming the two dimensional array of channels;
wherein a height of the first portion is greater than a height of the second portion.

17. The CT imaging system of claim 16 wherein each of the plurality of scintillator cells comprises a reflective material coated on a top surface thereof, the top surface of each scintillator cell being aligned with an edge of the reflective material coated on the honeycomb wall structure.

18. The CT imaging system of claim 16 wherein a height of the first portion is approximately 8 mm and a height of the second portion is approximately 3 mm.

19. The CT imaging system of claim 15 wherein the honeycomb wall structure is composed of a binder material and a powder material having a density and atomic number that is sufficient to substantially absorb x-rays.

20. The CT imaging system of claim 19 wherein the honeycomb wall structure comprises an extruded honeycomb wall structure formed from the binder material and the powder material.

21. The CT imaging system of claim 20 wherein the extruded honeycomb wall structure comprises a sintered honeycomb wall structure having a chemically polished finish.

* * * * *